(12) United States Patent  
Paul et al.

(10) Patent No.: US 8,003,778 B1  
(45) Date of Patent: *Aug. 23, 2011

(54) DETECTION OF RED TIDE ORGANISMS BY NUCLEIC ACID AMPLIFICATION

(75) Inventors: John H. Paul, St. Petersburg, FL (US); Mike Gray, St. Petersburg, FL (US); Erica Casper, St. Petersburg, FL (US)

(73) Assignee: University of South Florida, Tampa, FL (US)

( * ) Notice: Subject to any disclaimer, the term of this patent is extended or adjusted under 35 U.S.C. 154(b) by 0 days.

This patent is subject to a terminal disclaimer.

(21) Appl. No.: 12/724,854

(22) Filed: Mar. 16, 2010

Related U.S. Application Data (62) Division of application No. 10/707,747, filed on Jan. 8, 2004, now Pat. No. 7,700,278.

(60) Provisional application No. 60/319,841, filed on Jan. 8, 2003.

(51) Int. Cl.
*C07H 21/04* (2006.01)
(52) U.S. Cl. ...................................... 536/24.3
(58) Field of Classification Search ........................ None
See application file for complete search history.

(56) References Cited

U.S. PATENT DOCUMENTS

| | | | |
|---|---|---|---|
| 6,319,673 B1 | 11/2001 | Beck et al. | |
| 6,387,652 B1 | 5/2002 | Haugland et al. | |
| 6,395,517 B1 | 5/2002 | Abbaszadegan et al. | |
| 7,700,278 B1 * | 4/2010 | Paul et al. | 435/6 |
| 2003/0186222 A1 | 10/2003 | Paul, III | |

OTHER PUBLICATIONS

Leone, G., et al. 1998. "Molecular Beacon Probes Combined with Amplification by NASBA enable Homogeneous, Real-Time Detection of RNA." Nucleic Acids Research. vol. 26. No. 9. pp. 2150-2155.
Gray, M., et al. 2003. "Molecular Detection and Quantitation of the Red Tide Dinoflagellate *Karenia brevis* in the Marine Environment." Applied and Environmental Microbiology. vol. 69. No. 9. pp. 5726-5730.
Yoon, H. S., et al. 2002. "A Single Origin of the Peridinin-and Fucoxanthin-Containing Plastids in Dinoflagellates Through Tertiary Endosymbiosis." PNAS. vol. 99. No. 18. pp. 11724-11729.
Wilson, V. L., et al. 1999. "Species-Specific Detection of Hydrocarbon-Utilizing Bacteria." Journal of Microbiological Methods. vol. 39. pp. 59-78.
Bowers, H. A., et al. 2000. "Development of Real-Time PCR Assays for Rapid Detection of *Pfiesteria piscicida* and Related Dinoflagellates." Applied and Environmental Microbiology. vol. 66. No. 11. pp. 4641-4648.
Buck, G. A., et al. 1999. "Design Strategies and Performance of Custom DNA Sequencing Primers." BioTechniques. vol. 27. No. 3. pp. 528-536.

* cited by examiner

*Primary Examiner* — Kenneth R. Horlick
*Assistant Examiner* — David Thomas
(74) *Attorney, Agent, or Firm* — Michele L. Lawson; Smith & Hopen, P.A.

(57) ABSTRACT

A real-time reverse transcription-PCR, or NABSA, method (and associated primers) targeting the rbcL gene for the detection and quantitation of the Florida red tide organism, *Karenia brevis*.

7 Claims, 9 Drawing Sheets

| Species | Strain or Clone | Detection by real-time PCR | Species | Strain or Clone | Detection by real-time PCR |
|---|---|---|---|---|---|
| Positive controls | | | Praisinophytes | | |
| K. brevis | Apalachicola B5 | + | Tetraselmis sp. | 850001 | - |
| K. brevis | Apalachicola C6 | + | Tetraselmis sp. | CCMP961 | - |
| K. brevis | Charlotte Harbor A2 | + | Unidentified species | CCMP1536 | - |
| K. brevis | Charlotte Harbor C2 | + | Prymnesiophytes | | |
| K. brevis | Mexico Beach B3 | + | Isochrysis sp. | 3C | - |
| K. brevis | Mexico Beach C5 | + | Pavlova lutheri | CCMP1325 | - |
| K. brevis | Jacksonville C3 | + | Prymnesium parvum | NA | - |
| K. brevis | Piney Island A3 | + | Unidentified species | ST8CH26 clone | - |
| K. brevis | Piney Island B4 | + | Unidentified species | ST1CH3 clone | - |
| K. brevis | Wilson | + | Chlorophytes | | |
| Negative controls | | | Clamydomonas euryale | CCMP219 | - |
| Dinoflagellates | | | Unidentified species | ST5SY7 clone | - |
| K. mikimotoi | CCMP430 | - | Chlamydomonas sp. | ST2SY2 clone | - |
| Amphidinium carterae | CCMP1314 | - | Pycnococcus sp. | ST6SY8 clone | - |
| Akashiwo sanguinea | CCMP1321 | - | Cyanophytes | | |
| Alexandrium tamarense | CCMP1493 | - | Synechococcus sp. | CCMP836 | - |
| Glenodinium foliacrum | NAa | - | Synechococcus sp. | WH7803 | - |
| Gymnodinium catenatum | CCMP1937 | - | Synechococcus sp. | ST2SY26 clone | - |
| Gyrodinium sp. | NA | - | Prochlorococcus sp. | ST2SY33 clone | - |
| Kryptoperidinium foliaceum | NA | - | Trichodesmium sp. | ST8SY15 clone | - |
| Lingulodinium polyedra | CCMP1738 | - | Trebouxiophyte Chlorella autotrophica | CCMP243 | - |
| Prorocentrum micans | NA | - | | | |
| Scrippsiella trochoidea | NA | - | Coscinodicsophyte Thalassiosira pseudonana | CCMP1335 | - |
| Scrippsiella precaria | NA | - | Eustigmatophytes | | |
| Diatoms | | | Nannochloropsis sp. | ST3CH27 clone | - |
| Phaeodactylum tricornutum | CCMP1327 | - | Nannochloropsis sp. | ST1CH4 clone | - |
| Cylindrotheca sp. | ST6CH2 clone | - | Xanthophyte Heterococcus sp. | ST6CH33 clone | - |
| Skeletonema sp. | ST4CH31 clone | - | | | |
| Skeletonema sp. | ST4CH14 clone | - | | | |
| Raphidophyte Heterosigma akashiwo | NA | - | | | |

*KARENIA BREVIS* DETECTION USING REAL-TIME PCR 5729

DETECTION OF RED TIDE ORGANISMS BY NUCLEIC ACID AMPLIFICATION

CROSS REFERENCE TO RELATED APPLICATIONS

This application is a divisional application and claims priority to co-pending U.S. nonprovisional application Ser. No. 10/707,747, filed on Jan. 8, 2004, which is a nonprovisional of U.S. provisional application Ser. No. 60/319,841, filed on Jan. 8, 2003, which are incorporated herein by reference.

GOVERNMENT SUPPORT

This invention was made with government support under Grant No. NA160P1437 awarded by the National Oceanographic and Atmospheric Administration. The government has certain rights in the invention.

BACKGROUND OF THE INVENTION

*Karenia brevis* is an unarmored, non-peridinin-containing dinoflagellate that grows to ca. 20 to 40 µm in diameter. The organism is positively phototactic, is negatively geotactic, swims at a speed of ca. 1 m h$^{-1}$ and is thought to be an obligate photoautotroph. *K. brevis* is the causative agent of the recurring red tide blooms (21 of 22 years from 1975 to 1997) observed in the Gulf of Mexico and off the southeastern Atlantic coast of the United States, which have been reported since the Spanish conquests. Lipophilic brevetoxins produced by *K. brevis* can result in massive fish kills and have been implicated in the mortality of 700 bottlenose dolphins off the east coast of the United States in 1987 and the mysterious deaths of 149 Florida manatees in 1995 and 1996. In cases of human exposure, brevetoxin can cause respiratory distress by inhalation and food poisoning by consumption of tainted shellfish.

Current methods for the detection of *K. brevis* depend on microscopy or pigment analysis, methods which are time-consuming and require a considerable amount of expertise and skill. Isolation of dinoflagellates and cultivation from environmental samples to confirm identity may take months. Consequently, rapid molecular methods to detect *K. brevis* in the environment are needed.

SUMMARY OF INVENTION

The present invention is a method of detecting the presence of at least one dinoflagellate, specifically *K. brevis*, in a water sample comprising the steps of, identifying a unique gene sequence associated with the organism *K. brevis*, amplifying the unique gene sequence contained in the water sample using at least one purified primer, the primer having at least one *K. brevis* specific internal probe affixed thereto, the internal probe having a label attached thereto, and detecting the presence of the unique gene sequence within the sample.

Although many embodiments of the invention are contemplated, in one embodiment the amplification step is performed by reverse transcriptase polymerase chain reaction. When using reverse transcriptase polymerase chain reaction the unique gene sequence is a 91-base-pair region of the *K. brevis* rbcL gene. The purified primer sequence for real time reverse transcriptase polymerase chain reaction is SEQ ID NO: 1 (forward primer) and SEQ ID NO: 2 (reverse primer). The internal probe for real time reverse transcriptase polymerase chain reaction is SEQ ID NO: 3. Finally, the label attached to the internal probe is a fluorogenic compound and detection is achieved utilizing epiflouresence microscopy.

In another embodiment, the amplification step is performed by nucleic acid based amplification (NASBA). When using the NASBA method the unique gene sequence is an 87-base-pair region of the *K. brevis* rbcL gene. The purified primer sequence for nucleic acid sequence based amplification is SEQ ID NO: 4 (P1) and SEQ ID NO: 5 (P2). Finally, the internal probe (Beacon) for nucleic acid sequence based amplification is SEQ ID NO: 6.

BRIEF DESCRIPTION OF THE DRAWINGS

For a fuller understanding of the nature and objects of the invention, reference should be made to the following detailed description, taken in connection with the accompanying drawings, in which:

FIG. 1. indicates the positive and negative controls for amplification by real time RT_PCR.

BRIEF DESCRIPTION OF SEQUENCES

<110> University of South Florida
<120> DETECTION OF RED TIDE ORGANISMS BY NUCLEIC ACID AMPLIFICATION
<130> 1372.120PCR
<160> 8
<170> Patent In version 3.2
<210> 1
<211> 20
<212> DNA
<213> artificial sequence
<220>
<223> Forward primer designed to amplify and detect the 91-bp region of the rbcL gene specific to *K. brevis*.

<400> 1
tgaaacgtta ttgggtctgt 20
<210> 2
<211> 22
<212> DNA
<213> artificial sequence
<220>
<223> Reverse primer designed to amplify and detect the 91-bp region of the rbcl gene specific to K. brevis.
<400> 2
aggtacacac tttcgtaaac to 22
<210> 3
<211> 19
<212> DNA
<213> artificial sequence
<220>
<223> Fluorogenic probe designed to amplify and detect the 91-bp region of the rbcl gene specific to K. brevis.
<400> 3
ttaaccttag tctcgggta 19
<210> 4
<211> 19
<212> DNA
<213> artificial sequence
<220>
<223> Real Time NASBA primer (1) for the marker region of rbcL gene specific to K. brevis.
<400> 4
acgttattgg gtctgtgta 19
<210> 5
<211> 50
<212> DNA
<213> artificial sequence
<220>
<223> Primer (2) for real time NASBA to detect the marker region of the rcbL gene specific to K. brevis.
<400> 5
aattctaata cgactcacta tagggagaag gtacacactt tcgtaaacta 50
<210> 6
<211> 33
<212> DNA
<213> artificial sequence
<220>
<223> Molecular beacon used for real time NASBA assay.
<400> 6
cgatcgctta gtctcgggtt attttttcga tcg 33
<210> 7
<211> 19
<212> DNA
<213> artificial sequence
<220>
<223> PCR primer set was designed with sequence data from Karenia mikimotoi
(GenBank accession no. AB034635) by modifying existing chromophyte rbcL primers in order to amplify a 554-bp region (approximately one-third) of Karenia's rbcL gene.
<400> 7
atgatgaraa yattaactc 19
<210> 8
<211> 21
<212> DNA
<213> artificial sequence
<220>

<223> PCR primer set was designed with sequence data from Karenia mikimotoi (GenBank accession no. AB034635) by modifying existing chromophyte rbcL primers in order to amplify a 554-bp region (approximately one-third) of Karenia's rbcL gene.
<400> 8
atttgtcccg cattgattcc t 21

DETAILED DESCRIPTION OF THE PREFERRED EMBODIMENT

A molecular marker for this organism is ribulose-1,5-bisphosphate carboxylase/oxygenase (RuBisCO) large-subunit gene (rbcL). RuBisCO is the primary carbon-fixing enzyme in photoautotrophic organisms. *K. brevis* and the other fucoxanthin-containing dinoflagellates have a form ID rbcL enzyme, and genetic evidence suggests that they contain plastids of haptophyte origin acquired through tertiary endosymbiosis.

As rbcL is highly expressed in viable cells and mRNA levels can be orders of magnitude greater than those of DNA, the mRNA was targeted for this study. As RNA is rapidly degraded in the environment, an RNA target will give an indication of a viable population compared to what is detected by DNA-based methods, which may detect dead cells as well.

PCR Method

To obtain sequence data for this embodiment of the inventive method, a PCR primer set was designed with sequence data from Karenia mikimotoi (GenBank accession no. AB034635) by modifying existing chromophyte rbcL primers in order to amplify a 554-bp region (approximately one-third) of Karenia's rbcL gene (forward primer, ATGATGARAAYATTAACTC, (SEQ. ID NO. 7)); reverse primer, ATTTGT CCCGCATTGATTCCT, (SEQ. ID NO. 8), [International Union of Pure and Applied Chemistry degeneracy symbols were used]).

Cultures of *K. brevis* were obtained from the Florida Fish and Wildlife Conservation Commission's Florida Marine Research Institute. Strains were isolated by Marine Research Institute lab from the following locations around the Florida coast: Apalachicola, Charlotte Harbor, Mexico Beach, Jacksonville, and Piney Island. Strains used in this analysis were named for their isolation location and the plate well into which they were isolated. Several nontarget algal strains of diverse lineage were obtained from either the Provasoli-Guillard Center for Culture of Marine Phytoplankton (CCMP; West Booth-bay Harbor, Me.) or from the Steidinger lab (FIG. 1). All strains were under a 12-h-light-12-h-dark light regimen at 26 μmol $s^{-1}$ $m^{-2}$ and were incubated at 20 or 14° C. in F/2 medium, which was modified for each strain's needs according to CCMP's directions.

*K. brevis* cells are harvested by centrifugation (10 min at 5,000×g), and the DNA extracted by a modified phenol-chloroform method. PCR amplification is conducted with final concentrations of 1 μM for the primers, 3 mM for $MgCl_2$, 0.4 mM for each deoxynucleoside triphosphate, and 2.5 U of Taq polymerase (Promega Corp., Madison, Wis.). Cycling conditions are 40 repetitions of 95° C. for 1 min, 50° C. for 1 min, and 72° C. for 1.5 min, with a final extension step at 72° C. for 15 min. Amplification is confirmed by agarose gel electrophoresis. PCR amplicons are purified with a QIAquick PCR purification kit (QIAGEN, Valencia, Calif.) and ligated into the pCR II vector, and TOP10 cells transformed according to the manufacturer's instructions (Invitrogen Corp., Carlsbad, Calif.). Transformants are plated onto 2XYT plates containing 50 μg (each) of kanamycin and ampicillin per ml. White colonies are screened for insert size by PCR amplification. Positive clones are grown in 2XYT broth with antibiotics, and plasmid DNA extracted with a Wizard Plus SV miniprep spin kit (Promega Corp.). Clones from nontarget species from a rbcL clone library are also grown and extracted as described above. Sequencing of the 554-bp *K. brevis* and *K. mikimotoi* rbcL insert are performed at the DNA Sequencing Core laboratory at the University of Florida.

One of the sequenced clones carrying the 554-bp insert from *K. brevis* APC6 (clone 15) can be used in sensitivity testing. Nontarget environmental rbcL clones (from the same region of the gene) were obtained from the Gulf of Mexico during a previous study to initially test specificity (FIG. 1). Based on the direction of the insert, the vector is linearized by digesting the plasmid with either HindIII or EcoRV and a sense transcript made by in vitro transcription using the T7 or SP6 promoter site. The transcripts are purified with a QIAGEN RNeasy RNA extraction kit, with the DNase digestion step being performed according to the manufacturer's instructions. These transcripts are quantified with a Ribogreen RNA quantification kit according to the manufacturer's instructions (Molecular Probes, Inc., Eugene, Oreg.), mixed 1:1 with an RNA storage buffer (8 M guanidinium isothiocyanate, 80 mM Tris-HCl [pH 8.5], 24 mM $MgCl_2$, 140 mM KCl), aliquoted, and frozen at $-80°$ C. The *K. brevis* APC6 clone 15 transcript is used to generate real-time reverse transcription (RT)-PCR standard curves, while the others are used to test the specificity of the primer-probe set.

Figure 2:
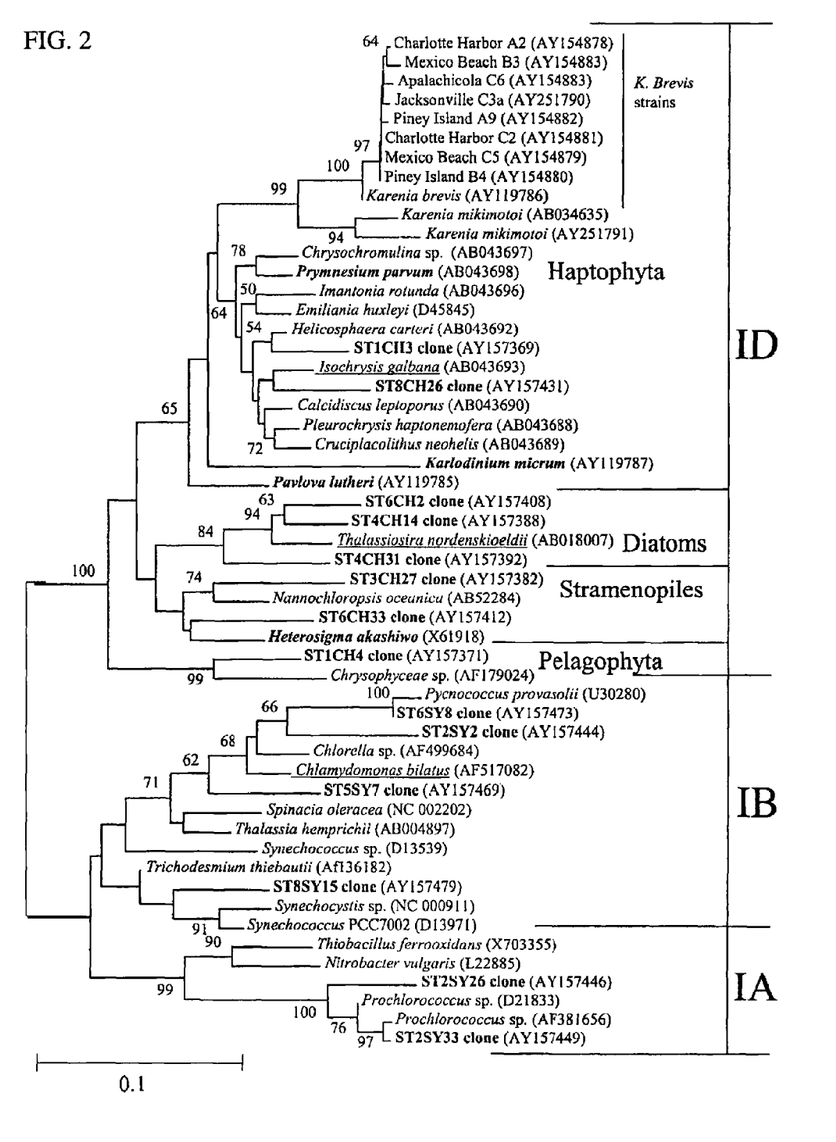
FIG. 2. shows a neighbor-joining phylogenetic tree based on deduced amino acid sequences with a Poisson distance correction showing relationships between form I rbcL sequences from *K. brevis* and other phytoplankton species, as well as clones obtained on a cruise to the Mississippi River plume in the Gulf of Mexico. Boldface taxa were tested by real-time RT-PCR as nontarget controls. There were many taxa tested as nontarget strains whose rbcL sequences were not available in GenBank, and closest sequenced representatives are underlined.

Sequences for phylogenetic comparison can be obtained from GenBank. During the course of experimentation, a sequence for *K. brevis* appeared in GenBank. Sequences were aligned and analyzed using the KODON software package, version 1.0 (Applied Maths, Inc., Austin, Tex.), which uses a Clustal W alignment method. Phylogenetic and molecular evolutionary analysis is conducted using MEGA2 software (version 2.1; S. Kumar, K. Tamura, I. B. Jakobsen, and M. Nei, Arizona State University, Tempe, 2001) using both nucleotide and deduced amino acid sequence data. All nontarget strains, their representative accession numbers, and their relationships based on deduced amino acid residues are shown in FIG. 2.

Sequence data from the *K. brevis* rbcL clones show a short (91-bp) region that is markedly different from *K. mikimotoi's* rbcL sequence. This portion of the rbcL gene of *K. brevis* has been selected as the target for a primer and probe set for the Taq-Man Taq nuclease assay. A primer set and an internal fluorogenic probe were designed to amplify and detect the 91-bp region (forward primer, TGAAACGTTAT-TGGGTCTGT, (SEQ. ID NO. 1); reverse primer, AGGTA-CACACTTTCGTAAACTA, (SEQ. ID NO. 2); internal probe, FAM [6-carboxyfluorescein]-TTAACCT-TAGTCTCG GGTA-TAMRA, (SEQ. ID NO. 3), [6-carboxytetramethylrhodamine]). For real-time RT-PCR, 5 µl of the target is added to 45 µl of a one-step RT-PCR mixture prepared from 2xRT-PCR TaqMan master mix (Applied Biosystems, Foster City, Calif.) containing each primer at a concentration of 1 µM, 2 mM MgCl, and a 0.5 µM concentration of the probe. Cycling conditions are as follows: a precycling reverse transcription step of $45°$ C. for 30 min; an initial denaturation step of $95°$ C. for 10 min; and then 40 cycles of $95°$ C. for 1 min, $55°$ C. for 1 min, and $72°$ C. for 1 min. Reaction mixtures run in the Applied Biosystems 7700 sequence detection system and are analyzed with their supplied software.

Cell counts for all cultured algal strains (including *K. brevis*) are carried out by filtering 1 ml of culture onto 0.22-µm-pore-size black polycarbonate Poretics filters (Osmonics Inc., Minnetonka, Minn.). Cells are counted by using epifluorescence microscopy on an Olympus BX-60 microscope with the 20Xobjective and blue excitation (filter set U-MNIB). RNA from the culture is extracted using the QIAGENRNeasy spin kit with the following modifications. Culture samples (1 ml) are filtered onto a 0.45-µm-pore-size HV polyvinylidene difluoride filter (Millipore Durapore). The filters are placed into 2-ml screw-cap microcentrifuge tubes containing 750 µl of RLT lysis buffer (QIAGEN) with 2-mercap-toethanol (10 µml). The filters are then incubated for 10 min at room temperature, 500 µl is removed into a 1.5-ml microcentrifuge tube, and RNA extraction continued according to the manufacturer's instructions (QIAGEN). The extracted RNA can be quantified using a Ribogreen RNA quantification kit according to the manufacturer's instructions. All nontarget algal strains are tested for amplification with the real-time primer-probe set with 10 pg of nontarget RNA per reaction mixture.

Field samples were collected by the Florida Marine Research Institute from several locations at several different times in Collier County (west coast of Florida; collected 28 March, 2 and 9 April, and 2 May 2003) and from the Indian River lagoon (east coast of Florida; collected 13 Dec. 2002) during both bloom and nonbloom events. Algae in field samples were counted by microscopy by the Florida Fish and Wildlife Conservation Commission prior to our receiving them. Algae from field samples were extracted as described above, but 10 to 20 ml was extracted and 5 µl of the extract was added to the RT-PCR mixture.

The TaqMan probe-based RT-PCR assay (91-bp amplicon) yields only positive results with *K. brevis* strains (FIG. 2). All other dinoflagellates (including *K. mikimotoi*) and algal strains resulted in no amplification. All strains tested were present in sufficient concentrations to allow for amplification based on the lowest detectable concentration of *K. brevis*.

Figure 3:
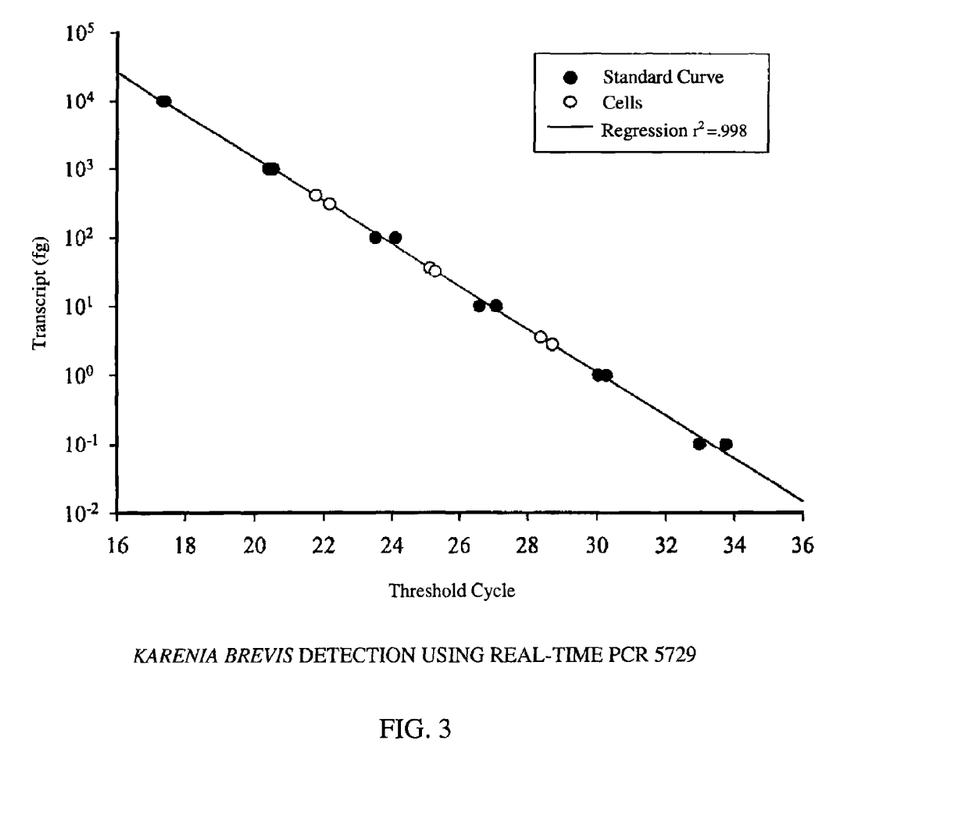
FIG. 3. depicts a real-time RT-PCR standard curve generated from the APC6 clone 15 transcript showing the linearity of the method, covering 7 orders of magnitude (filled circles [trendline]). Also shown are amplification results from *K. brevis* cellular extracts corresponding to 100 cells, 10 cells, and 1 cell per reaction (open circles).

Standard curves derived by using the in vitro transcript from APC6 clone 15 show sensitivity over a range of concentrations spanning 7 orders of magnitude, ranging from 0.1 fg to 1,000 pg, as shown in FIG. 3. Standard curves using whole-cell extracts from *K. brevis* culture are sensitive to as little as 1 pg of total RNA (less than 1 cell per reaction, based on cell counts and dilution).

Figure 4:
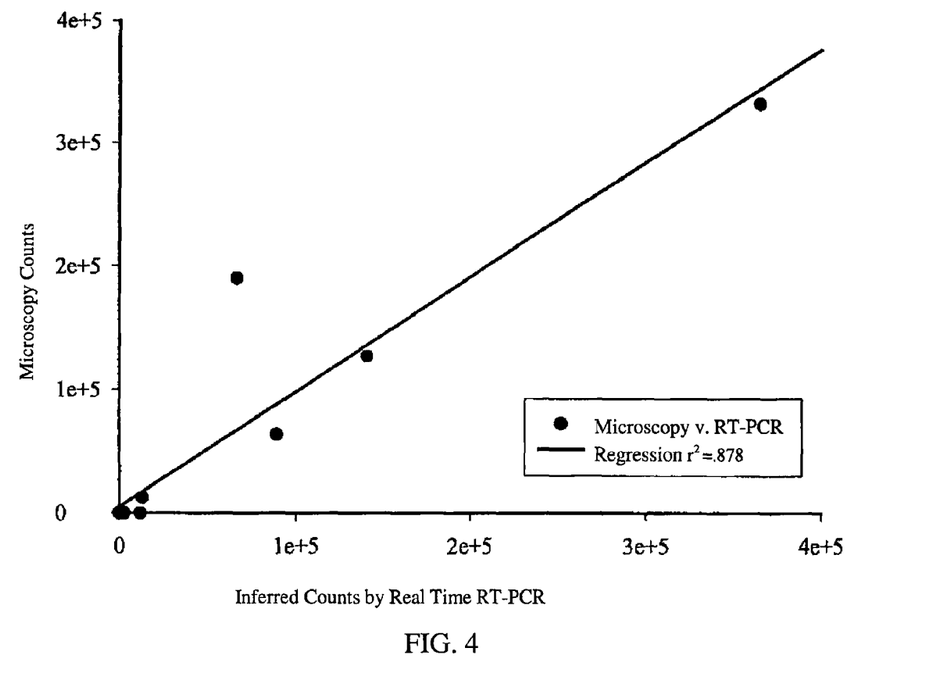
FIG. 4 shows a comparison of microscopy cell counts and real-time RT-PCR-inferred cell counts from natural bloom samples.

Red tide bloom and nonbloom samples from around Florida were analyzed for *K. brevis* using this method. From the west coast, 15 samples were analyzed; 11 were nonbloom and 4 were moderate to high bloom. The two samples from the east coast were composed of one bloom and one nonbloom. Microscopy counts of the nonbloom samples were below the detection limit of 333 cells liter$^{-1}$. Counts inferred by RT-PCR were mostly 0.0 cell liter or below the detection limit by microscopy (7 of 12 samples). Of the remaining five nonbloom samples, three gave a result of approximately 1,000 cells liter$^{-1}$, one indicated 3,000 cells liter$^{-1}$, and one indicated 12,000 cells liter$^{-1}$. The last sample's result may be due to contamination of the sample. For the bloom samples, all but one indicated that cell density was very close to that of the microscopy counts, and one sample indicated approximately one-third the density by microscopy. As this method targets mRNA, it is possible that the cells in the last sample were not producing high levels of transcript or that they were no longer viable. FIG. 4 summarizes this comparison of cell densities for these field samples as enumerated by microscopy and inferred from real-time RT-PCR. A good correlation ($r^2=0.878$) was observed between the results of both methods for field samples.

Using the TaqMan probe, it is possible to amplify and detect a wide range of concentrations of *K. brevis* to the exclusion of all nontarget DNA and RNA tested, with a detection limit of less than 100 cells liter$^{-1}$ when 20 ml of seawater is extracted. When larger volumes are filtered, lower detection limits should be attainable. The dynamic range over which this technique is effective covers the range of natural *K. brevis* blooms in the environment. When an environment contains <1,000 cells liter$^{-1}$ (as determined by microscopy cell counts), *K. brevis* is considered to be present but poses no risk of adverse health effects or shellfish contamination. Samples with >1,000 cells liter$^{-1}$ are considered to have a very low level bloom, carrying a slight risk of respiratory irritation. At concentrations of >5,000 cells liter$^{-1}$ shellfish harvesting is closed. The highest level of a bloom has been reached when there are >10$^6$ cells liter$^{-1}$. A bloom of this magnitude can result in massive fish kills, respiratory distress in humans, and discoloration of the water and can affect the health of marine mammals such as dolphins and manatees.

NASBA Method

Figure 5:
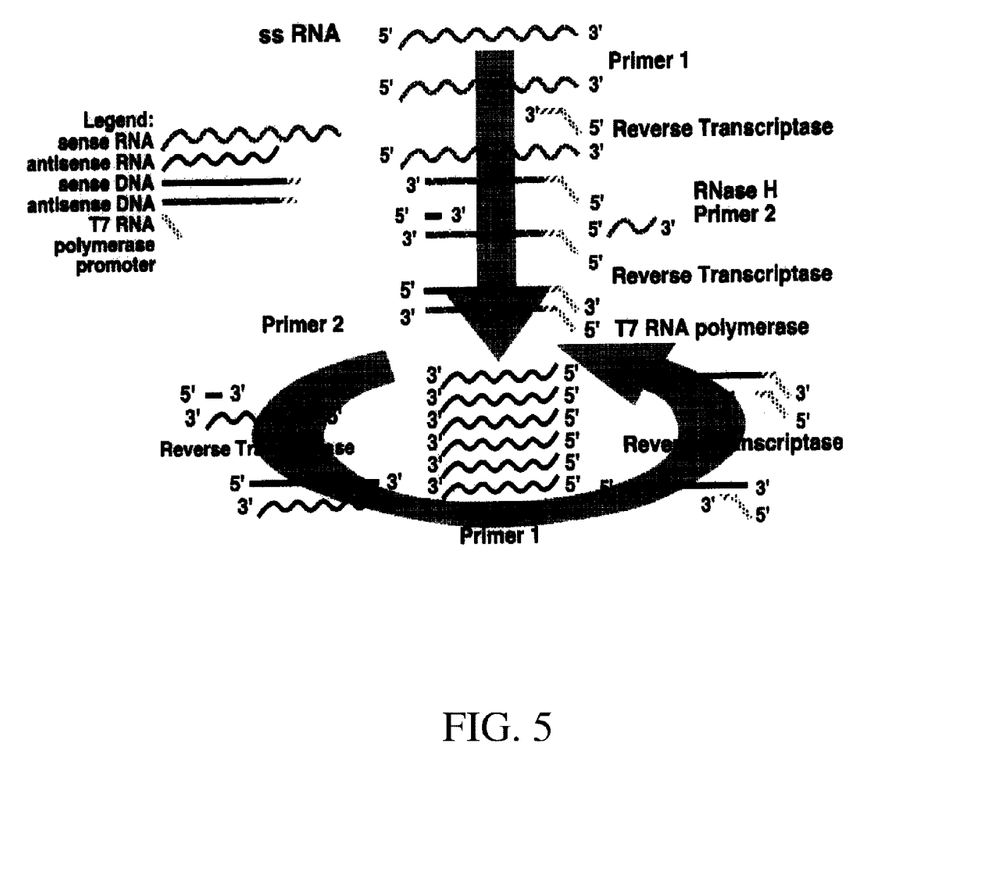
FIG. 5 is a graphic representation of the nucleic acid sequence based amplification (NASBA) pathway.

Nucleic acid sequence-based amplification (NASBA) (FIG. 5), is an isothermal method of RNA amplification (Davey and Malek, 1989). At a fixed temperature of 41° C., RNA is amplified by use of an enzyme cocktail consisting of T7 RNA polymerase, AMV reverse transcriptase, and RnaseH and two target specific oligonecleotide primers. Primer P1 (SEQ. ID NO. 4), which contains T7 RNA polymerase promoter hybridizes to the target RNA and a cDNA is made by the AMV reverse transcriptase. This results in the production of a DNA/RNA hybrid. RnaseH digests the RNA, leaving a single strand of antisense DNA. Primer 2 (SEQ. ID NO. 5) then binds to the DNA and is elongated, yielding a double stranded DNA molecule with an intact T7 RNA polymerase promoter sequence. From this double stranded product, many copies of single stranded antisense RNA are transcribed. This antisense RNA serves as the template for a new cycle of amplification, though the primers bind in reverse order.

Figure 6:
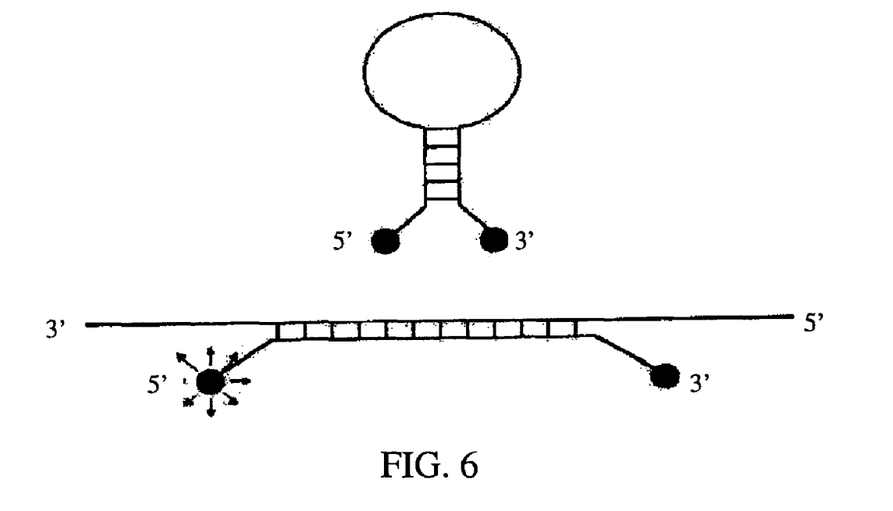
FIG. 6 is an illustration of a molecular beacon. Unbound the quencher (3') prevents the dye (5') from fluorescing. Once bound to the amplicon, the dye and quencher are separated and the dye gives off a fluorescent signal.

In this embodiment of the inventive method, real time detection of the amplicon is accomplished by use of a molecular beacon (SEQ. ID NO. 6) labeled with 6-carboxy fluorescein (6-FAM) at its 5' end and quencher DABCYL at its 3' end (FIG. 6). The beacon forms a stem-loop structure. The loop sequence is complementary to the target sequence and two complementary stem sequences are added to each side of the loop. When bound to amplicon, the quencher is separated from the fluorescein, and the probe fluoresces. The fluorescent signal is measured and the time at which it reaches a threshold of detection is measured. The time it takes a sample to reach the threshold is a function of how much initial target RNA is in the sample.

NASBA primers for detection of *K. brevis* are designed to target an 87 base pair sequence of the ribulose 1,5-bisphosphate carboxylase-oxygenase large subunit (rbcL). Standard curves and sensitivity are determined with in vitro transcript as well as with whole cells from culture. Specificity is assessed using non-target environmental rbcL clones and environmental isolates. Sequence information for rbcL of clones and isolates are obtained from GenBank and nucleotide sequences are aligned using the ClustalW algorithm (Thompson et al., 1994) in Kodon v1.0 (Applied Maths Inc, Austin Tex.). Amino acid sequences deduced from the nucleotide sequences were compared and a phylogenetic tree was created by performing neighbor joining with 1000 bootstrap replications in the MEGA v2.1 (Kumar et al., 1993) software package.

Cells from culture and natural seawater samples are filtered onto sterile Millipore Durapore 0.45 µm filters prior to RNA extraction via the RNeasy Kit from Qiagen. The filters are submerged in the Qiagen supplied RLT lysis buffer for 10 minutes. After incubation the buffer is recovered and the RNeasy protocol followed.

*Karenia brevis* cultures and natural seawater samples were obtained from the staff at the Florida Marine Research Institute (FMRI). Natural seawater samples were collected by a variety of agencies in Southwest Florida as part of a regular monitoring program. Non-target organisms were obtained from B. Richardson (FMRI) and the Provasoli-Guillard National Center for Culture of Marine Phytoplankton (CCMP). Environmental clones were supplied by B. Wawrik (University of South Florida).

Figure 7:
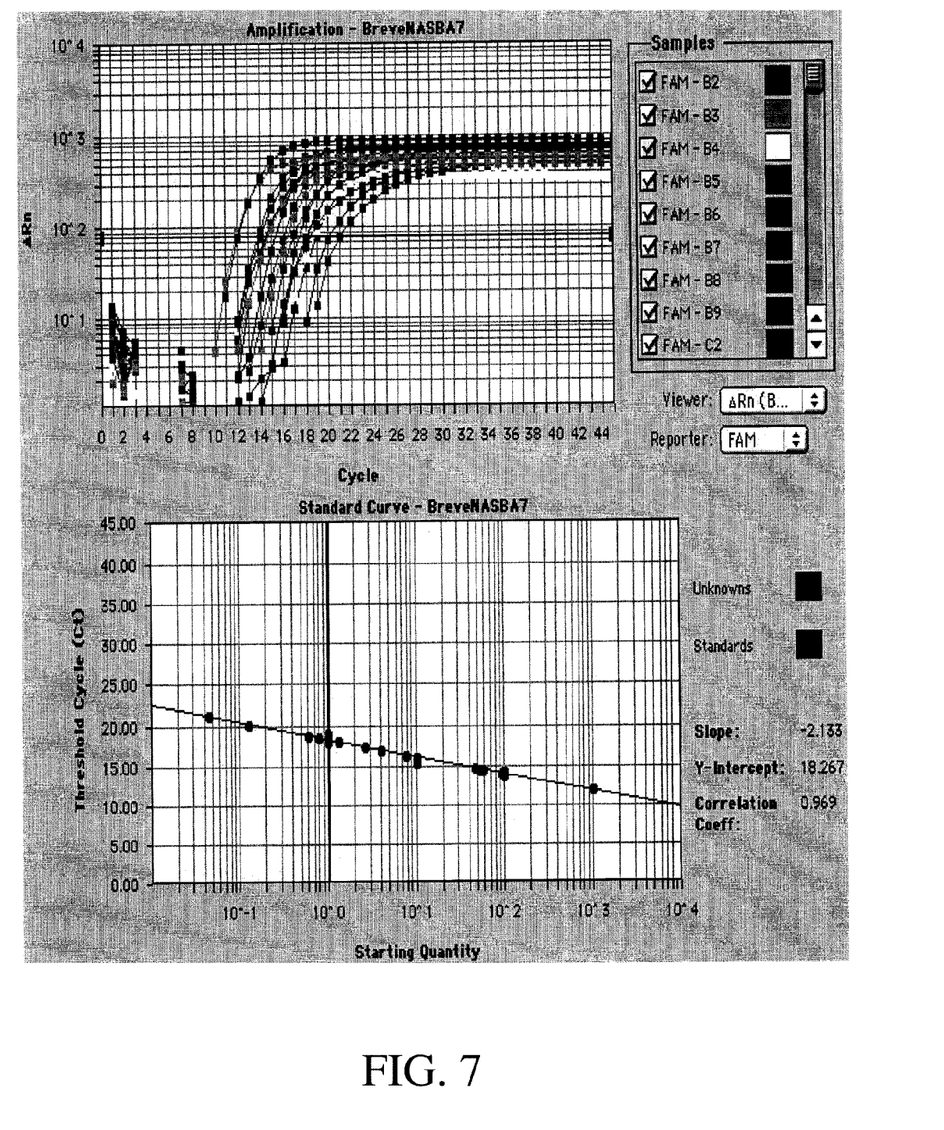
FIG. 7 represents the real time amplification plot and standard curve of *K. brevis*. Standard curve was generated from 10$^3$, 10$^2$, 10, and 1 fg transcript RNA. Unknowns are a combination of cultured cells and bloom samples containing varying numbers of *K. brevis*.
Figure 8:
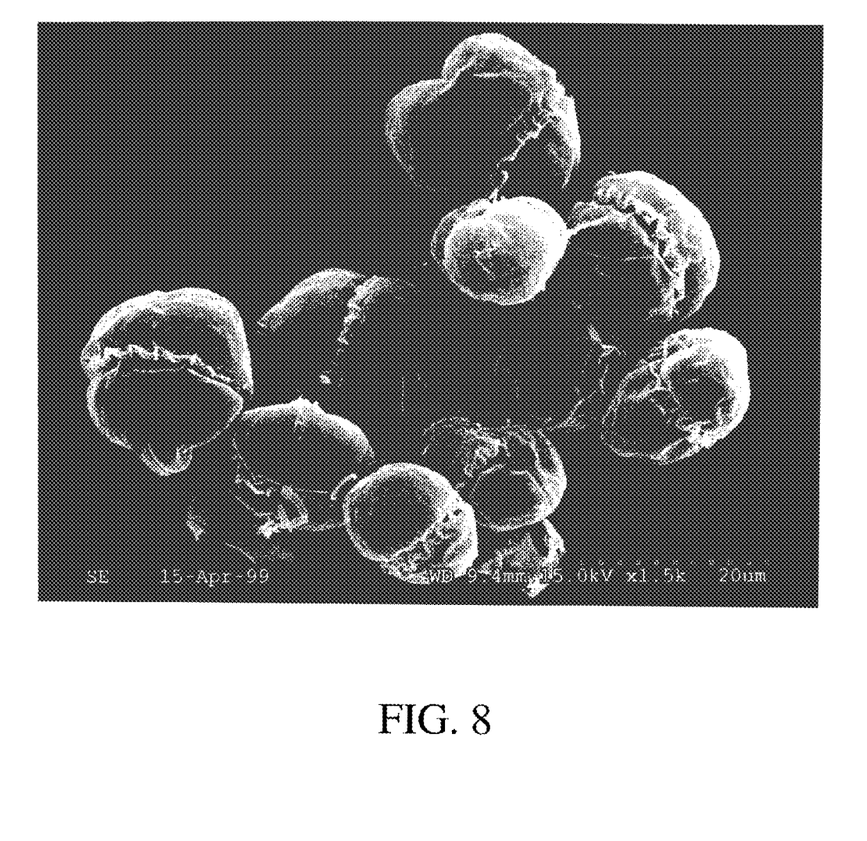
FIG. 8 is an EM photograph of *K. brevis*.

As a result of the inventive method:

Amplification of cultured cells occurred in about 15 minutes (FIG. 7).

The assay was sensitive to as little as one *K. brevis* cell and to date can detect 1 fg in vitro transcript.

*Karenia brevis* was detected in natural seawater samples collected where blooms had been reported.

The NASBA assay did not result in detection of non-target organisms and environmental clones.

This embodiment of the inventive method is a real time NASBA assays for the detection and quantification of marine enteroviruses and *K. brevis*. This assay can routinely detect 100 viral particles and can detect as little as one *K. brevis* cell. NASBA is a rapid and sensitive method for detection of RNA, and can be applied to a variety of organisms. NASBA is used in clinical settings to detect a variety of microorganisms, including HIV, hepatitis, *Salmonella*, and *E. coli*, among many others. NASBA has also been used to detect other microorganisms in aquatic environments. This embodiment of the inventive method is the first to apply NASBA to the detection of *K. brevis* from marine waters.

NASBA is both rapid and sensitive and is less technologically demanding than other molecular detection methods. Advantages of using NASBA include its isothermal nature and rapid, real time detection. Rapid detection of these microorganisms is important from both human health and economic standpoints. These assays are being developed with the eventual goal of being used in the field (at sea or in coastal waters) with the assistance of personnel or being deployed on an autonomous sensor platform (moored buoy or autonomous underwater vehicle). This technology is important as it will enable the rapid detection, identification, and quantification of microorganisms in coastal waters, For Real Time NASBA, the following primers and molecular beacon are used:

BreveNASBA1—5'-ACGTTATTGGGTCTGTGTA-3'
BreveNASBA2—5'-AATTCTAATACGACTCACTAT-AGGGAGA-AGGTACACACTTTCGTAAACTA-3'
BreveBEACON—5'-FAM-CGATCGCT-TAGTCTCGGGTTATTTTTTCGATCG-DABCYL-3'

Figure 9:
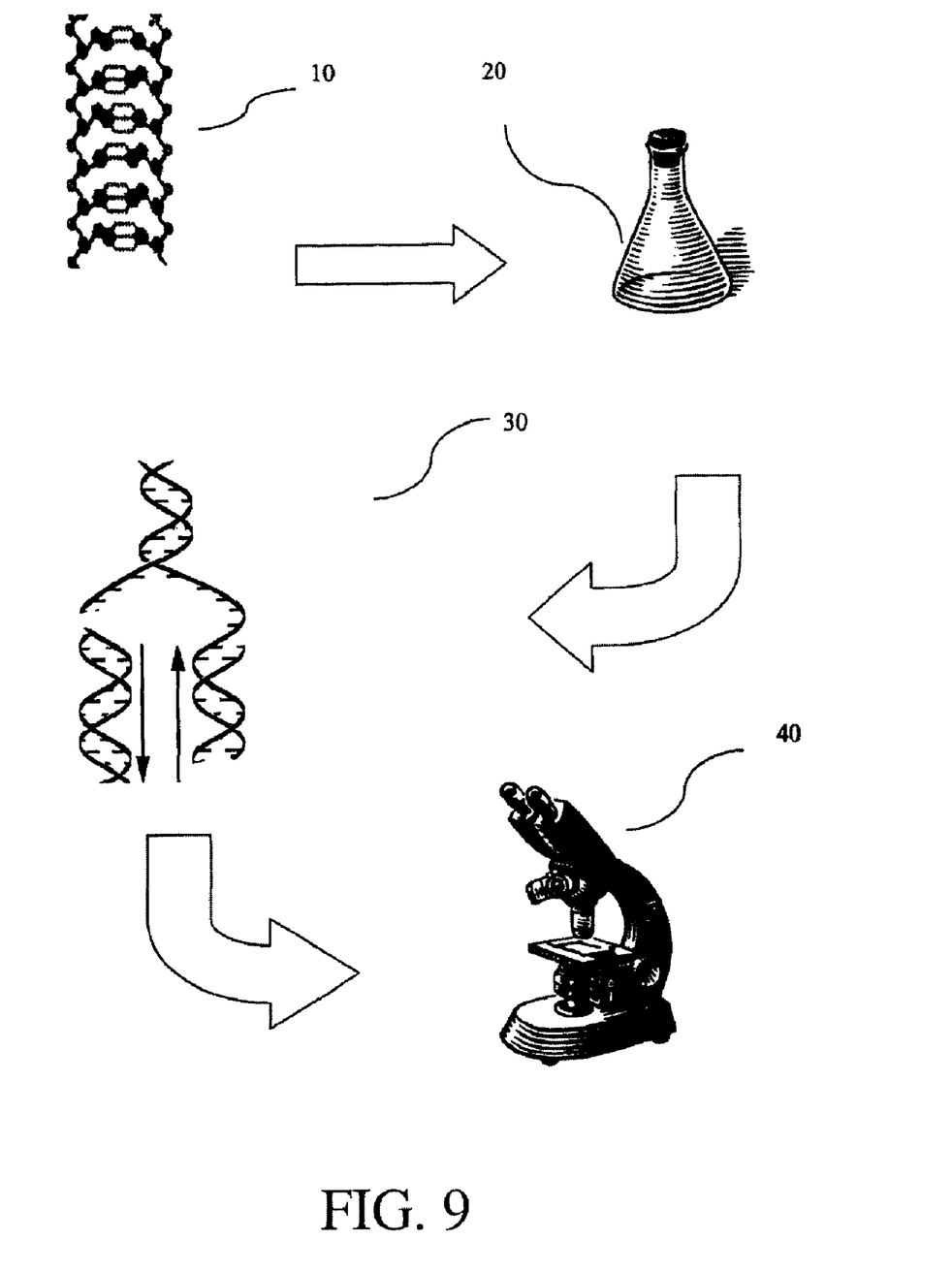
FIG. 9 is a graphic representation of the inventive method.

FIG. 9 is a graphic representation of the inventive method. First the unique gene sequence is identified 10. Then a water sample is taken 20. The target gene sequence is amplified, by either polymerase chain reaction or nucleic acid sequence based amplification, using the specific primers and probes 30. After the amplification process is complete the sample is tested for the presence of the amplified sequence 40.

These methods represent the first molecular detection strategies for *K. brevis*, and are well suited for the detection and monitoring of red tide blooms caused by *K. brevis* in the Gulf of Mexico and the southern Atlantic coast of the United States. Although diel regulation of rbcL in *K. brevis* has not been characterized, this assay provides an easy and relatively rapid procedure that might be employed as an alternative to the more difficult and time-consuming methods currently used by red tide monitoring and management programs in Florida and other states affected by K. brevis.

It will be seen that the objects set forth above, and those made apparent from the foregoing description, are efficiently attained and since certain changes may be made in the above construction without departing from the scope of the invention, it is intended that all matters contained in the foregoing description or shown in the accompanying drawings shall be interpreted as illustrative and not in a limiting sense.

It is also to be understood that the following claims are intended to cover all of the generic and specific features of the invention herein described, and all statements of the scope of the invention which, as a matter of language, might be the to fall therebetween. Now that the invention has been described,

---

SEQUENCE LISTING

<160> NUMBER OF SEQ ID NOS: 8

<210> SEQ ID NO 1
<211> LENGTH: 20
<212> TYPE: DNA
<213> ORGANISM: artificial sequence
<220> FEATURE:
<223> OTHER INFORMATION: Forward primer designed to amplify and detect
      the 91-bp region of the rbcL gene of K. brevis.

<400> SEQUENCE: 1
tgaaacgtta ttgggtctgt                                                    20

<210> SEQ ID NO 2
<211> LENGTH: 22
<212> TYPE: DNA
<213> ORGANISM: artificial sequence
<220> FEATURE:
<223> OTHER INFORMATION: Reverse primer designed to amplify and detect
      the 91-bp region of the rbcl gene specific K. brevis.

<400> SEQUENCE: 2
aggtacacac tttcgtaaac ta                                                 22

<210> SEQ ID NO 3
<211> LENGTH: 19
<212> TYPE: DNA
<213> ORGANISM: artificial sequence
<220> FEATURE:
<223> OTHER INFORMATION: Fluorogenic probe designed to amplify and
      detect the 91-bp region of the rbcl gene specific K. brevis.

<400> SEQUENCE: 3
ttaaccttag tctcgggta                                                     19

<210> SEQ ID NO 4
<211> LENGTH: 19
<212> TYPE: DNA
<213> ORGANISM: artificial sequence
<220> FEATURE:
<223> OTHER INFORMATION: Real Time NASBA forward primer for the marker
      region of rbcL gene specific to K. brevis.

<400> SEQUENCE: 4
acgttattgg gtctgtgta                                                     19

<210> SEQ ID NO 5
<211> LENGTH: 50
<212> TYPE: DNA
<213> ORGANISM: artificial sequence
<220> FEATURE:
<223> OTHER INFORMATION: Reverse primer for real time NASBA to detect
      the marker region of the rcbL gene specific to K. brevis.

<400> SEQUENCE: 5
aattctaata cgactcacta tagggagaag gtacacactt tcgtaaacta                   50

```
<210> SEQ ID NO 6
<211> LENGTH: 33
<212> TYPE: DNA
<213> ORGANISM: artificial sequence
<220> FEATURE:
<223> OTHER INFORMATION: Molecular beacon used for real time NASBA
      assay.

<400> SEQUENCE: 6
cgatcgctta gtctcgggtt attttttcga tcg                                33

<210> SEQ ID NO 7
<211> LENGTH: 19
<212> TYPE: DNA
<213> ORGANISM: artificial sequence
<220> FEATURE:
<223> OTHER INFORMATION: PCR primer set was designed with sequence data
      from Karenia mikimotoi (GenBank accession no. AB034635) by
      modifying existing chromphyte rbcL primers in order to amplify a
      554-bp region (approximately one-third) of Karenia's rbcL gene
      (forward

<400> SEQUENCE: 7
atgatgaraa yattaactc                                                19

<210> SEQ ID NO 8
<211> LENGTH: 21
<212> TYPE: DNA
<213> ORGANISM: artificial sequence
<220> FEATURE:
<223> OTHER INFORMATION: PCR primer set was designed with sequence data
      from Karenia mikimotoi (GenBank accession no. AB034635) by
      modifying existing chromphyte rbcL primers in order to amplify a
      554-bp region (approximately one-third) of Karenia's rbcL gene
      (reverse

<400> SEQUENCE: 8
atttgtcccg cattgattcc t                                             21
```

What is claimed is:

1. A pair of forward and reverse oligonucleotide primers for use in the amplification-based detection of *K. brevis* wherein said primers amplify a target region of the ribulose 1,5-biphosphate carboxylase-oxygenase large subunit (rbcL) of *K. brevis* and do not amplify DNA from *K. mikimotoi*.

2. A pair of forward and reverse oligonucleotide primers for detecting the presence of *K. brevis*, comprising:
   a first primer comprising a base sequence SEQ. ID. No. 1; and
   a second primer comprising a base sequence SEQ. ID. No. 2.

3. The primer pair of claim 2 wherein the first primer is a forward primer.

4. The primer pair of claim 2 wherein the second primer is a reverse primer.

5. The primer pair of claim 2, further comprising a probe comprising a base sequence SEQ. ID. No. 3.

6. A pair of forward and reverse oligonucleotide primers for detecting the presence of *K. brevis*, comprising:
   a first primer comprising a base sequence SEQ. ID. No. 4; and
   a second primer comprising a base sequence SEQ. ID. No. 5.

7. The primer pair of claim 6, further comprising a beacon comprising a base sequence SEQ. ID. No. 6.

* * * * *